United States Patent [19]
Wiles et al.

[11] Patent Number: 5,686,731
[45] Date of Patent: Nov. 11, 1997

[54] MULTI-PARAMETER SCANNING SYSTEM WITH MOVEABLE FIELD MASK

[75] Inventors: Gregory R. Wiles, Royal Oak; Charles C. Prain, III, Oxford, both of Mich.

[73] Assignee: ATI Systems, Inc., Madison Heights, Mich.

[21] Appl. No.: 640,027

[22] Filed: Apr. 30, 1996

[51] Int. Cl.⁶ .................................................. G01N 21/86
[52] U.S. Cl. .................... 250/559.22; 250/559.45; 250/234; 356/376
[58] Field of Search ............... 250/559.22, 559.27, 250/559.28, 559.4, 559.41, 559.45, 559.49, 234; 359/225, 227, 738–739; 356/376, 380, 382, 430–431; 369/44.23, 44.24, 118

[56] References Cited

U.S. PATENT DOCUMENTS

| 4,818,108 | 4/1989 | Eppinger | 356/376 |
| 5,051,575 | 9/1991 | Hino | 250/559.22 |

*Primary Examiner*—Que Le
*Attorney, Agent, or Firm*—Gifford, Krass, Groh, Sprinkle, Patmore, Anderson & Citkowski, P.C.

[57] ABSTRACT

An apparatus for scanning the visual characteristics of a surface includes an illumination system which scans a beam of light across the surface for reflection therefrom. The reflected beam is split into two parts. A first part goes to a control sensor which generates a control signal in response to the spatial distribution of the intensity of the reflected light. A second portion of the reflected light goes to a measuring sensor. A field mask is disposed in the beam of reflected light and operates to restrict the cross-sectional area of the beam which impinges upon the measuring sensor. Positioning of the field mask is controlled by a driver responsive to the control signal produced by the control sensor. In this manner, the field mask may be positioned so as to select only specularly reflected light for measurement. The system may also be operated to move the field mask in accord with a preselected program so as to determine the slope of the intensity of the reflected light, and this slope may be utilized to calculate the haze value of the surface being inspected.

18 Claims, 3 Drawing Sheets

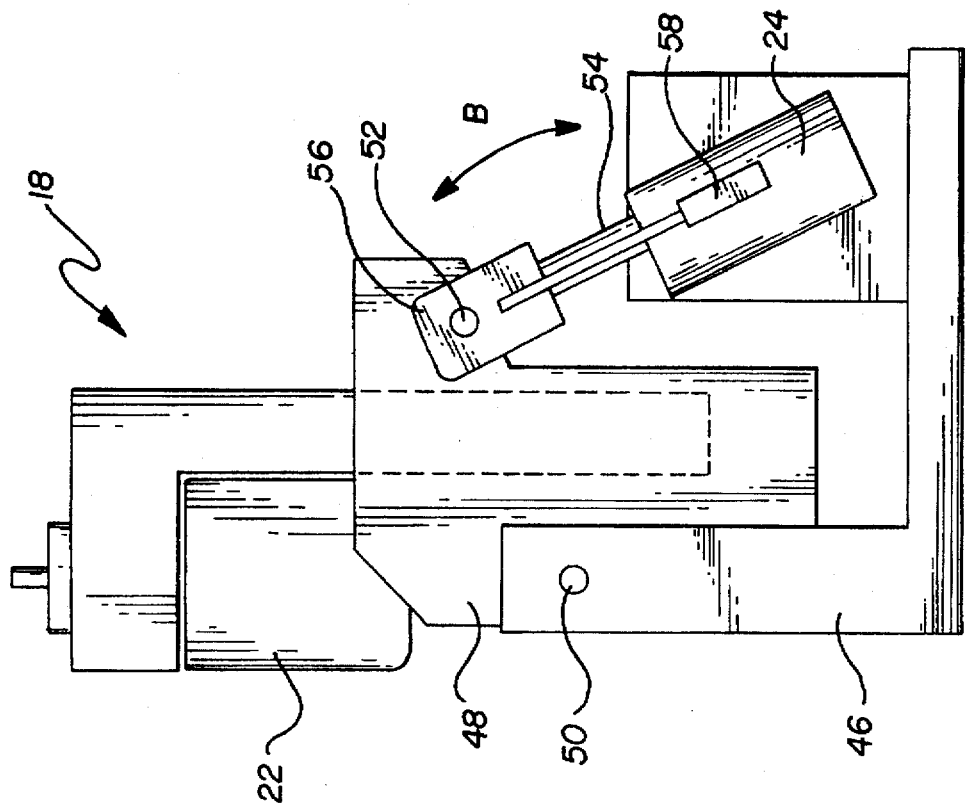
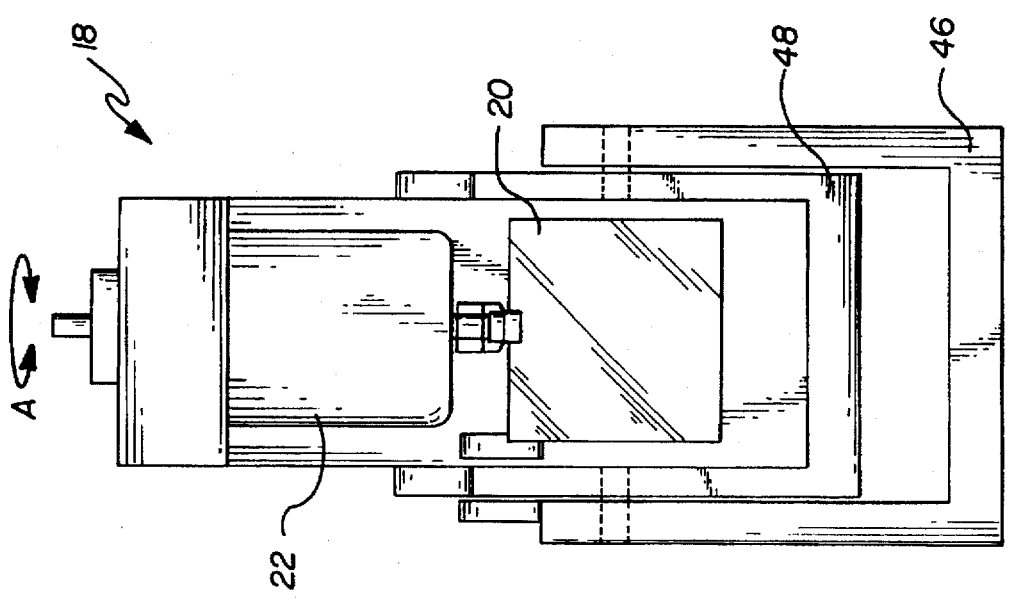

MULTI-PARAMETER SCANNING SYSTEM WITH MOVEABLE FIELD MASK

FIELD OF THE INVENTION

This invention relates generally to systems for inspecting and characterizing surfaces. More specifically, the invention relates to optical systems in which a beam of light is scanned across a surface, and a number of parameters indicative of surface quality are measured on the basis of the reflection of the scanned beam.

BACKGROUND OF THE INVENTION

It is often necessary to measure the surface characteristics of painted, plated, polished or otherwise finished objects in the course of their manufacture. The visual appearance of a finished surface is a highly subjective determination; however, a number of parameters have been established in the art to quantify aspects of surface quality. Among the measurements which are commonly made are distinctness of image (DOI), which is a measure of how clearly an object is reflected by a surface; gloss, which is a measurement of the dispersion with which light is reflected from a surface; orange peel, which is a surface characteristic dependent upon the presence of surface features having a texture in the general size range of 0.5 to 1.0 millimeter, which produce a texture appearing somewhat reminiscent of the skin of an orange; tension, which is a measurement of the clarity with which a projected grid pattern is reflected from a surface; and haze (also referred to as texture), which is a measurement of the clarity with which the image of an object is reflected from the surface. There is overlap in the quantities which are measured by these various determinations, and various manufacturers will rely upon different ones of these parameters. In many instances, these parameters are assessed subjectively by comparing a finished surface with a series of standards. In other instances, various algorithms have been developed for calculating these parameters, based upon the reflection of light from the surface. For example, some particular techniques for the measurement of gloss and distinctness of image are disclosed in U.S. Pat. No. 4,761,676.

In a manufacturing environment, it is generally desirable to have an automated system for quantifying the aforementioned parameters of surface quality. Such equipment should be rugged enough to withstand operation in a production facility or quality control laboratory. The equipment should also be reliable, low in cost and simple to use and maintain. It is further desirable that the equipment be capable of being used in a noncontact mode. A number of systems have been developed in the prior art for the inspection or characterization of finished surfaces. U.S. Pat. No. 4,853,879 discloses a scanning system which includes a number of sensors for measuring different parameters of surface quality. U.S. Pat. No. 4,918,321 discloses a specialized, large system which projects a strip of light onto a motor vehicle, and analyzes the reflection of that strip of light to assess surface quality. U.S. Pat. No. 4,199,219 discloses a system which employs a specialized lens to select only that light reflected from inclined portions of a surface for analysis. U.S. patent application Ser. No. 08/426,973 entitled "Apparatus for Measuring Optical Characteristics of a Surface" discloses a particular apparatus for measuring the orange peel characteristics of a finished surface.

One problem encountered with many prior art surface characterization systems is that the optical geometry thereof requires precise alignment of the surface and measuring apparatus. This requirement presents problems when irregular surfaces are being inspected, and requires a degree of precision which is difficult to obtain in a manufacturing environment. In many instances, surfaces are finished with paint containing metal flakes. These metal flakes present a number of randomly disposed, highly reflective surfaces, and it has been found that a number of prior art systems are "confused" by spurious reflections from these metal flaked surfaces.

There is a need for a system which can reliably and accurately characterize a variety of finished surfaces on the basis of optical reflection therefrom. The system should be capable of determining a full range of surface characteristics, and should be simple to use and maintain. As will be described in greater detail hereinbelow, the present invention provides an optical system which fulfills these criteria.

BRIEF DESCRIPTION OF THE INVENTION

There is disclosed herein an apparatus for measuring the visual characteristics of a surface. The apparatus includes an illumination system which comprises a light source for providing an incident beam of light and a scanner. The scanner includes a mirror disposed to intercept the incident beam of light and direct it onto a surface to be characterized so as to produce a reflected beam of light therefrom. The scanner further includes a scan mechanism for moving the mirror so as to scan the beam across a surface. The apparatus also includes: a measuring system which has a beam splitter disposed, and operative, to intercept the reflected beam of light and split it into a first portion and a second portion; a position sensitive control sensor which is disposed and operative to intercept the first portion of the reflected beam and generate a control signal which corresponds to a spatial profile of the first portion, and a measuring sensor which is disposed, and operative, to intercept said second portion of the reflected beam and generate an output signal corresponding to the second portion. The measuring system further includes a field mask interposed in the reflected beam between the surface and the measuring sensor. The field mask defines an aperture which permits a segment of the cross-sectional area of the reflected beam to pass therethrough to the measuring sensor. Finally, the measuring system includes a tracking driver which is operative to receive the control signal from the control sensor and spatially displace the field mask in response to that signal so as to selectably pass only a segment of the cross-sectional area of the reflected beam onto the measuring sensor.

In one embodiment, the scanner is configured so as to direct the incident beam of light onto the surface to be characterized at a right angle thereto. In another embodiment, the field mask and control sensor are both mounted onto a single member and the tracking driver is operative to spatially displace that member so as to move the control sensor and field mask as a single unit. When the control sensor and field mask are mounted to move as a single unit, the tracking driver and control sensor can establish a feedback loop wherein the tracking driver displaces the control sensor relative to the first portion of the reflected beam and thereby maintains a preselected spatial relationship between that first portion of the beam and the control sensor. In one particular embodiment, the tracking driver is operative to spatially displace the field mask so as to selectably pass only specularly reflected light therethrough.

In another aspect of the invention, there is provided a scan assembly for directing an incident beam of light along a two-dimensional path. The scan assembly includes a base member, a mirror and first electromagnetic actuator having the mirror pivotally supported thereby. The first electromagnetic actuator is operable, when activated, to pivot the mirror about a first axis of rotation. The scanner further includes a gimbal linkage pivotally coupling the first electromagnetic actuator, and the associated mirror, to the base through a second pivot axis disposed at a right angle to the first pivot axis. A second electromagnetic actuator is in mechanical communication with the gimbal linkage and operates, when activated, to pivot the first electromagnetic actuator and mirror about the second pivot axis. A position indicator may be associated with the second electromagnetic actuator, and in some instances the position sensor comprises a linear potentiometer.

In yet another aspect of the present invention there is provided a method for determining the haze of a finished surface. The method includes the steps of providing a light source and projecting a beam of light from the source onto a surface to be characterized. The incident beam is reflected from the surface and provides a reflected beam of light having a cross-sectional area. The method involves the further step of disposing a photo sensor in the reflected beam, and the photo sensor is operative to provide an output signal proportional to the intensity of illumination incident thereupon. A field mask is interposed in the reflected beam between the surface and the photo sensor. The field mask has an aperture defined therethrough which has an area which is less than the cross-sectional area of the beam. The field mask is moved transversely through the reflected beam so as to sequentially pass portions of the cross-section of the reflected beam therethrough and onto the photo sensor, whereby the photo sensor generates an output which changes as the intensity of the sequential, cross-sectional portions of the reflected beam vary. In a final step, the rate of change of the output signal of the photo sensor is determined, and this rate of change is proportional to the haze value of the surface being characterized.

BRIEF DESCRIPTION OF THE DRAWINGS

FIG. 4 is a front elevational view of a scanner structured in accord with the principles of the present invention;

FIG. 5 is a side elevational view of the scanner of FIG. 2; and

DETAILED DESCRIPTION OF THE INVENTION

Figure 1:
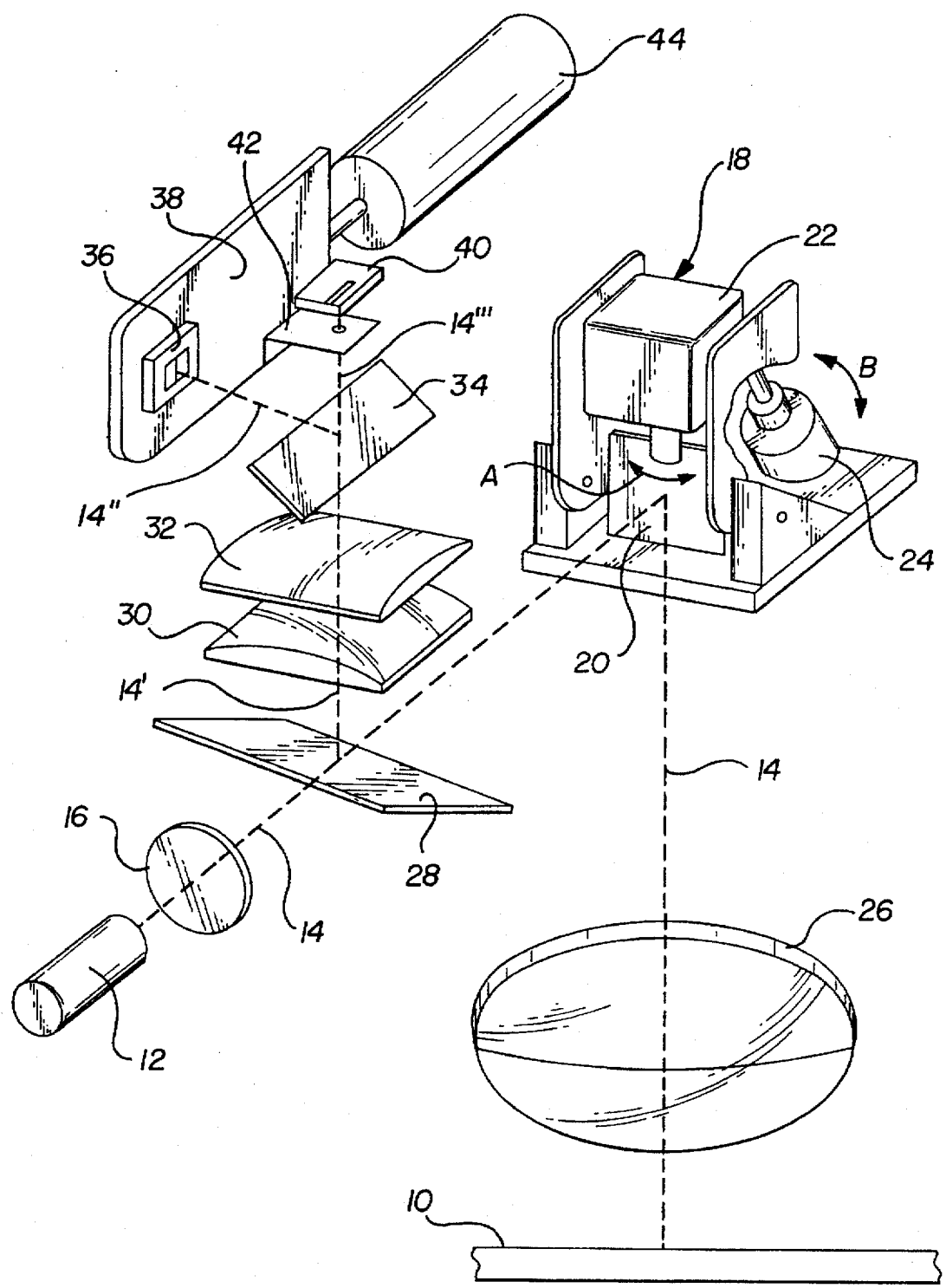
FIG. 1 is a schematic depiction of one apparatus structured in accord with the principles of the present invention as operative for measuring the visual characteristics of a surface.

The present invention is directed to a simple, reliable apparatus which may be employed to measure a number of different optical characteristics of a surface on the basis of the reflection of light from that surface. The apparatus of the present invention may be implemented in a variety of configurations, in accord with the principles disclosed herein. Referring now to FIG. 1, there is shown a schematic depiction of the optical system of one apparatus structured in accord with the principles of the present invention, as operative to measure the optical characteristics of a reflective surface 10.

As depicted, the apparatus includes an illumination system which is operative to scan a beam of light across the surface 10 being characterized. The illumination system includes a light source, which in this instance is a laser 12, preferably a solid state Ga-As laser; although it is to be understood that different light sources, including other lasers, may be similarly employed. The light source 12 provides a beam of light 14 which is focused by an optional lens 16. The illumination system further includes a scanner 18 operative to direct a beam of light 14 onto the surface 10, and to scan that beam thereacross. In the illustrated embodiment, the scanner 18 is a two axis scanner, as will be described in greater detail hereinbelow, and it is operative to scan the light beam 14 in a two-dimensional pattern across the surface 10.

Specifically, the scanner 18 includes a mirror 20 disposed so as to be pivoted about a first axis of rotation, as indicated by arrow A, by means of a galvanometer drive 22. The scanner 18 includes a second driver 24, which in this instance is a linear stepper, which operates to pivot the mirror 20, as well as the associated galvanometer 22 about a second axis, as indicated by arrow B, in a direction generally orthogonal to the first direction A. In this manner, the beam of light 14 is scanned across the surface 10 through a two-dimensional area. As shown in FIG. 1, a lens 26 is disposed between the mirror 20 and surface 10, and functions to collimate the beam of light 14, and to collect light reflected from the surface 10. Again, it is to be understood that this lens 26 is an optional element and may be eliminated, or substituted for by other optical elements.

In the illustrated embodiment, the light source 12 and scanner 18 are positioned relative to the surface 10 so that the incident beam of light 14 strikes the surface 10 at an approximate right angle. While the present system may be implemented in conjunction with various geometries, it has been found that by illuminating the surface 10 at an approximate right angle, the geometry of the optical system of the present invention may be simplified. It is a notable feature of the present invention that the particular configuration of its apparatus allows for accurate measurements of gloss, haze and other such optical parameters through the use of an incident light beam which illuminates the surface under characterization at approximate right angles. This is in contrast to prior art measuring systems which must typically measure gloss, and other optical parameters, at an angle of illumination which is 10° or 20° off normal.

Since, in the illustrated embodiment, illumination is normal to the surface 10, the reflected beam of light 14' retraces the path of the incident beam 14 back to the scanner mirror 20. A first beam splitter 28 is disposed in the optical path so as to intercept the reflected beam 14' and direct it to the measuring portion of the apparatus of the present invention. As illustrated, the beam splitter 28 is a partially silvered mirror, although it is to be understood that the beam may be otherwise redirected, as for example by a rotating mirror, a holographic element or the like.

As illustrated, a pair of cylindrical lenses 30, 32, are disposed in the reflected beam 14, at right angles to one another. These cylindrical lenses 30, 32 aid in shaping the cross-sectional area of the reflected beam 14'. Other optical elements such as spherical lenses, holographic optical elements and the like may be similarly employed, while in other instances it may be found unnecessary to include such optical elements.

A second beam splitter 34 is disposed in the reflected beam 14, and is operative to divide the reflected beam 14 into a first portion 14" and a second portion 14'''. The system includes a control sensor 36, disposed upon a support member 38, and positioned so as to be illuminated by the first portion 14" of the reflected beam. The control sensor 36 is preferably a bi-segmented, position sensitive photo sensor which provides an output signal corresponding to the spatial pattern of the incident illumination. One particularly preferred sensor is sold by the Advanced Photonics Corporation under the designation I L 10.

A measuring sensor 40 is disposed in the second portion 14''' of the reflected beam. This sensor 40 is operative to generate an output signal corresponding to the intensity of the illumination incident thereupon. One particularly preferred sensor is sold by the Silicon Detector Corporation under the designation 113-24-21. The output from the measuring sensor 40 may be processed, as shall be further detailed hereinbelow, or in accord with methods known in the art to provide data indicative of the surface characteristics.

In accord with the present invention a field mask 42 is disposed in the reflected beam, between the surface 10 and the measuring sensor 40. As illustrated herein, the field mask 42 is disposed in relatively close proximity to the measuring sensor 40. The field mask 42 includes an aperture defined therein, and is operative to restrict the cross-sectional area of the reflected beam which is incident upon the measuring sensor 40.

The field mask 42 is capable of being spatially displaced so as to selectably pass a particular cross-sectional portion of the reflected beam therethrough and onto the measuring sensor 40. As illustrated in FIG. 1, the field mask 42 is mounted onto the same support member 38 as is the control sensor 36. The support 38 is selectably displaceable by means of a tracking driver 44, which comprises a servo motor. The tracking driver 44 is responsive to the output signal produced by the control sensor 36, and repositions the field mask 42 in accord therewith so as to selectably pass only a particular portion of the reflected beam onto the measuring sensor 40.

In the illustrated embodiment, a feedback loop is established between the control sensor 36 and tracking driver 44, via a controller (not shown), whereby the tracking driver 44 moves the support member 38, and associated control sensor 36 and field mask 42 so as to maintain the first portion 14" of the reflected beam 14 in a preselected spatial relationship with the position sensitive control sensor 36. In this manner, the field mask 42 is likewise moved so as to permit the selectable illumination of the measuring sensor 40.

It has been found in accord with the present invention that by inclusion of the controllable field mask, accuracy of the measuring system is greatly improved, and accurate measurements may be made on surfaces which include irregularities such as metal flakes. Also, through the use of the present invention, the accuracy of measurements made with an incident beam normal to the surface are very accurate and correlate with measurements made off axis, as for example at 10° or 20° from normal. Preferably, the field mask 42 is positioned so as to pass only that portion of the incident beam which represents specular reflection on to the measuring sensor. In general, the specularly reflected portion of the beam will constitute the most intense portion; therefore, by controlling the position of the support member 38 so as to maximize the output of the control sensor 36, the field mask 42 will be positioned so as to admit mostly specularly reflected light to the measuring sensor 40.

Figure 2:
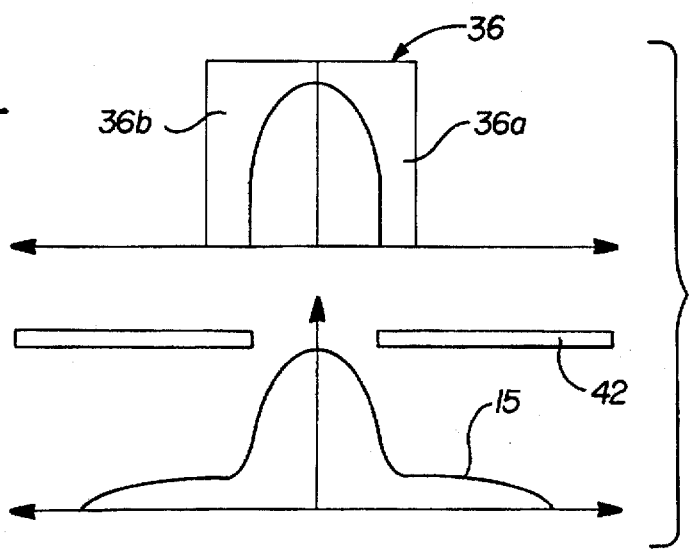
FIG. 2 is a schematic depiction of the operation of the field mask and control sensor of the present invention to select the specular component of a reflected beam of light including a specular and a diffuse component.
Figure 3:
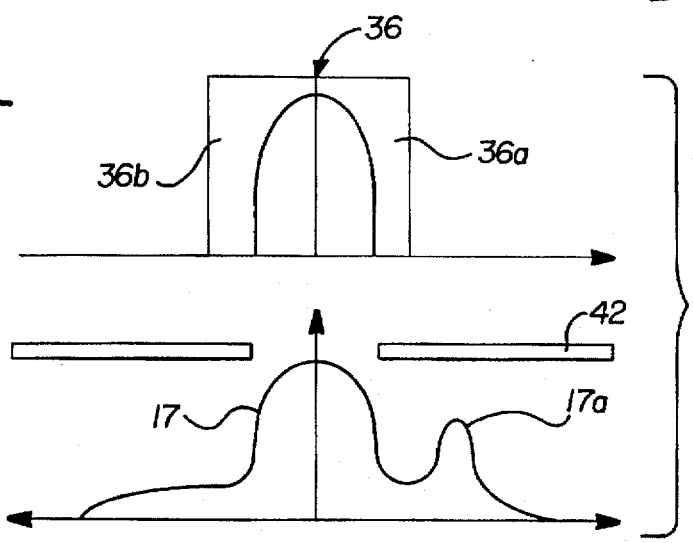
FIG. 3 is a schematic depiction of the operation of the field mask and control sensor of the present invention to select the major specular component of a reflected beam of light which includes a major specular component, a minor specular component and a diffuse component.

The operation of the field mask and control sensor of the FIG. 1 embodiment, for purposes of selecting a specular portion of a reflected beam of light, is shown schematically in FIGS. 2 and 3. Referring now to FIG. 2, there is shown a curve 15 which depicts the intensity profile of a beam of light which has been reflected from a painted surface and which includes a highly specular component thereof. Curve 15 shows the intensity of the reflected light along the vertical axis and the spatial distribution of the light along the horizontal axis. As will be noted the curve 15 includes a central portion of relatively high intensity which has a fairly narrow spatial distribution, superimposed upon a broader, lower intensity curve. The central, high intensity portion corresponds generally to specularly reflected light while the broad, low intensity reflection corresponds to diffuse reflected light.

Also shown in FIG. 2 is a field mask 42 having an opening defined therethrough. The opening is positioned, in the FIG. 2 embodiment, to pass the central portion of the specularly reflected light therethrough and onto a control sensor 36. As depicted, the control sensor 36 is comprised of two separate segments 36a, 36b, each of which constitutes a photodetector. The sensor 36 is positioned so that the two segments 36a, 36b are equally illuminated by the specular portion of the beam of light which passes through the field mask 42. Accordingly, it will be understood that the output of the two segments 36a, 36b will be equal when the specular portion of the reflected light is centered on the detector 36. By comparing the outputs from each of the segments 36a, 36b, a control signal indicative of proper positioning of the detector 36 will be generated. This control signal may be employed to control the movement of the field mask 42 (and in the embodiment of FIG. 1, the movement of the control sensor 36). In this manner, a feedback loop is established and the field mask 42 and sensor 36 track the specular portion of the reflected light.

In those instances where the reflected light includes a specularly reflected component which is smaller relative to the diffusely reflected component, than is shown in FIG. 2, the system illustrated therein will still operate in the same manner. In such instance, the control sensor 36 will still be operable to produce a usable control signal when the output thereof is indicative of illumination of the sensor 36 with light which is of maximum intensity, and equal on the two segments 36a, 36b. In this manner, the field mask 42 may be controlled so as to select a segment of the reflected light including a specular component.

Referring now to FIG. 3, there is shown the operation of a system generally similar to that of FIG. 2, in the instance where the reflected beam of light being analyzed comes from a painted surface having a loading of metal flake particles therein. FIG. 3 depicts a curve 17 showing the spatial distribution of the intensity of illumination from said metal flake painted surface. The curve 17 includes a first component resultant from specular reflection from the painted surface. This specularly reflected portion corresponds generally in shape and position to that shown in FIG. 2. It is further notable that the curve of FIG. 3 includes a second, somewhat smaller portion 17a which is the result of specular reflection from oriented metal flake material in the body of the paint. This component is of lower intensity than the main, specularly reflected portion.

In the FIG. 3 embodiment, the field mask 42 is positioned so as to pass only the main specularly reflected portion of the light on to the control sensor 36 so as to provide equal illumination on the two segments 36a, 36b thereof. By controlling the field mask 42 so as to illuminate the control sensor 36 with light such that illumination of the two segments 36a, 36b is both equal and maximized, the main, specularly reflected portion of the light will be selected.

While the FIG. 2 and 3 embodiments depict control sensors having two segments, it is to be understood that the invention may be practiced with sensors having a single segment or a larger number of segments. For example, a single segment sensor may be moved, in combination with the field mask so as to select a maximum level of illumination incident thereupon whereby specular illumination will be selected. In other instances, the control sensor may include more than two segments. For example, the control sensor may be a multiple segment sensor providing an output signal for carrying positional information, and this positional information may be employed to move a field mask, independently of the sensor, so as to appropriately guide a specular component of reflected light onto a measuring sensor. All of such embodiments are within the scope of the present invention.

While the field mask 42 and control sensor 36 are depicted as being mounted onto a single support member 38, it is to be understood that other arrangements may be implemented in accord with the present invention. For example, the control sensor 36 may be separately mounted, and may or may not be repositionable by the tracking driver 44. In one instance, the control sensor 36 may comprise a position sensitive two-dimensional array which will effectively determine the spatial profile of the reflected beam, and provide a control signal which may be employed by a tracking driver to move the field mask 42 into the specularly reflected portion of the beam. In other instances, the control sensor may simply measure total intensity and illumination incident thereupon, and the system operated to maximize the intensity of illumination on the sensor. Other such modifications and variations will be readily apparent to one of skill in the art. It is a notable feature of the present invention that by inclusion of a field mask under the active control of a system responsive to the spatial profile of the reflected beam, accuracy and utility of the system are greatly improved.

Although not illustrated, it is to be understood that the control functions may be readily implemented utilizing a general purpose computer, a programmable logic controller, or hard wired circuitry. In general, the control system for positioning the field mask will be relatively simple, and will basically constitute a servo feedback loop which moves the control sensor and mask, or an open loop system which relies upon positional signals generated by the control sensor to direct repositioning of the mask. All of such modifications and variations are within the scope of the present invention.

In accord with the present invention, there has been developed a particularly configured scan assembly for directing a beam of illumination along a two-dimensional path onto the surface to be characterized. Referring now to FIGS. 4 and 5, there is shown one particular embodiment of this scan assembly 18. FIG. 4 is a front elevational view of the scan assembly 18. The assembly includes a base portion 46 configured to support the remaining elements of the scan assembly, and to facilitate mounting of the scan assembly into the measuring apparatus of the present invention. The base member 46 pivotably supports a gimbal linkage 48 which in turn supports a first electromagnetic actuator, in this instance a galvanometer 22, which in turn has a mirror 20 supported thereby. The galvanometer actuator 22 operates to pivot the mirror 20, in a reciprocal manner, about a first axis of rotation, as indicated by arrow A. It is to be understood that the illustrated combination of planar mirror and galvanometer 22 may be replaced by equivalent optical elements, such as a multi-segmented mirror rotatably supported by an electrical motor or the like.

Referring now to FIG. 5, there is shown a side elevational view of the scanner 18. As will be seen from FIG. 3, the base 46 supports the gimbal linkage 48 through a pivot point 50. The galvanometer 22 is in turn supported by the gimbal linkage 48. Shown in FIG. 5 is a second electromagnetic actuator, which in this instance comprises a linear stepper 24. The linear stepper 24 is in turn supported by the base 46, and is pivotably connected to the gimbal linkage 48 by a connector link 56, through a second pivot axis 52. The linear stepper 24 is operative, in response to an electrical input, to incrementally advance and withdraw a shaft 54, and by so doing will cause the gimbal linkage 48 to pivot about pivot point 50, as indicated by arrow B.

A position indicator is preferably included with the second actuator, to monitor the degree to which the gimbal linkage 48 is pivoted, and in the illustrated embodiment, the position sensor comprises a linear potentiometer 58 associated with the stepper 24. In operation, the combination of pivoting actions provided by the first 22 and second 24 actuator, will cause the mirror 20 to reflect an incident beam of light along a two-dimensional scan pattern.

Figure 6:
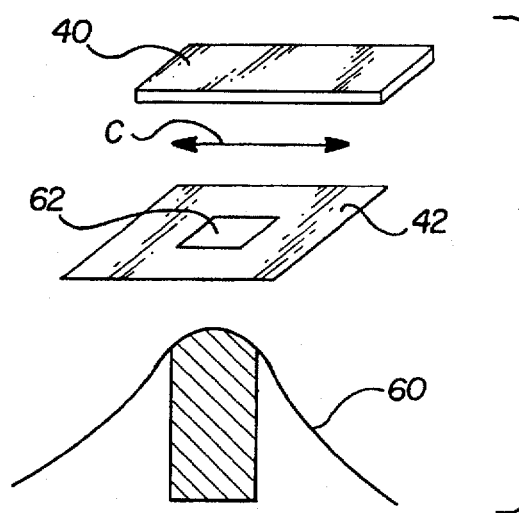
FIG. 6 is a schematic depiction of the implementation of a measuring methodology for determining haze, in accord with the present invention.

Referring now to FIG. 6, there is shown a schematic depiction of a field mask 42, together with a gaussian curve 60 which depicts the intensity profile of a beam of light as reflected from a surface under analysis. The gaussian distribution is typical of one pattern of reflected light encountered in the use of the present invention and as was explained with reference to FIGS. 2 and 3, is a result of the fact that some portion of the light is specularly reflected by the surface under analysis, while another portion of the light is diffusely reflected by the surface. Also, some of the light may be specularly reflected at an off-axis angle because of the presence of metal flakes and the like on the surface of the object being scanned. It will be noted from FIG. 6 that the field mask 42 includes a relatively small aperture 62 defined therein. By appropriately positioning the aperture 62 selected portions of the reflected beam may be directed to a photo sensor 40. As indicated by arrow C, the field mask 42 may be displaced so as to sample different portions of the gaussian distribution of light intensity represented by curve 60.

In order to determine gloss of the surface, the mask 42 is positioned to primarily permit specular light as indicated by the shaded area 60a under curve 60, to strike the detector 40, and since gloss is defined as the intensity of the specular reflection from a surface, the detector 40 will provide a signal proportional to the shaded are 60a under the curve, which signal is indicative of the gloss of the surface.

Applicant has further found that the optical arrangement depicted in FIG. 6 may be utilized to determine haze of a surface by moving the field mask 42 so as to successively sample light intensity at different portions of the gaussian curve 60. A very hazy surface will scatter large amounts of light producing a broad, flat gaussian distribution, whereas a low haze surface will produce a very sharp distribution. In accord with the present invention, haze may be measured by moving the field mask, as indicated by arrow C, and determining the slope of the intensity curve 60. The slope will be inversely proportional to haze.

In a typical haze determination, the system depicted in FIG. 1 is operated to scan the incident beam of light across the surface under investigation, and the tracking driver 44 is operated independently of the position sensor 36 so as to move the field mask 42 in a direction generally transverse to the scan direction so as to sample the intensity profile of the reflected beam. In this manner, the detector 40 produces a changing signal indicative of the slope of the intensity of the beam, which signal may be readily correlated with a haze measurement.

The apparatus of the present invention is capable of providing surface quality measurements utilizing a beam of light incident at 90° upon a surface. The system can operate in a noncontact mode and is capable of rapidly scanning a large, two-dimensional area of a surface. It has been found that measurements made with the present apparatus correlate extremely well with those made by slower, most expensive systems of the type employed in the prior art.

While the present invention has been described primarily with reference to one particular optical system, it is to be understood that in view of the teaching herein, modifications and variations of the system will be readily apparent to those of skill in the art. The foregoing drawings, discussion and description are illustrative of one particular embodiment of the invention and are not meant to be limitations upon the practice thereof. It is the following claims, including all equivalents, which define the scope of the invention.

We claim:

1. An apparatus for measuring the visual characteristics of a surface including:
    A. An illumination system comprising:
        a light source for providing an incident beam of light; and
        a scanner including a mirror disposed to intercept said incident beam of light and direct it onto a surface to be characterized so as to produce a reflected beam of light therefrom, said scanner further including a scan mechanism for moving said mirror so as to scan said incident beam across said surface; said apparatus further including:
    B. A measuring system comprising:
        a beam splitter disposed and operative to intercept said reflected beam and split it into a first portion and a second portion;
        a control sensor which is disposed and operative to intercept the first portion of said reflected beam and generate a control signal which corresponds to a spatial profile of said first portion;
        a measuring sensor which is disposed and operative to intercept said second portion of said reflected beam and generate an output signal corresponding to said second portion;
        a field mask interposed in said reflected beam, between said surface and said measuring sensor, said field mask defining an aperture which permits only a segment of the cross-sectional area of said reflected beam to pass therethrough and be incident upon said measuring sensor; and
        a tracking driver which is operative to receive said control signal and spatially displace said field mask in response thereto so as to selectably pass only a segment of the cross-sectional area of said reflected beam onto said measuring sensor.

2. An apparatus as in claim 1, wherein said scanner is disposed so as to direct said incident beam of light onto said surface at a right angle thereto.

3. An apparatus as in claim 1, wherein said field mask and said control sensor are both mounted on a single member and said tracking driver is operative to spatially displace said member so that said control sensor and field mask move as a single unit.

4. An apparatus as in claim 3, wherein said tracking driver and control sensor establish a feedback loop wherein said tracking driver displaces said control sensor, relative to the first portion of said reflected beam, so as to maintain a preselected spatial relationship between said first portion and said control sensor.

5. An apparatus as in claim 1, wherein said field mask is interposed in the second portion of said reflected beam.

6. An apparatus as in claim 1, wherein said tracking driver is operative to spatially displace said field mask to as to selectively pass only specularly reflected light therethrough.

7. An apparatus as in claim 1, wherein said tracking driver is operative to displace said field mask so as to only pass the most intense portion of said reflected beam therethrough.

8. An apparatus as in claim 1, wherein said tracking driver includes a servo motor.

9. An apparatus as in claim 1, wherein said control sensor is a multi-segmented photo sensor.

10. An apparatus as in claim 1, wherein said light source is a laser.

11. An apparatus as in claim 1, wherein said scan mechanism is operative to pivot said mirror about an axis of rotation.

12. An apparatus as in claim 1, wherein said scan mechanism is operative to pivot said mirror about two axes of rotation so as to scan said beam across said surface in two dimensions.

13. An apparatus as in claim 12, wherein said scan mechanism includes a galvanometer for pivoting the mirror about said first axis and a microstep actuator for pivoting the mirror about said second axis.

14. An apparatus as in claim 13, further including a position sensor associated with said microstep actuator.

15. An apparatus as in claim 14, wherein said position sensor is a linear potentiometer.

16. An apparatus for measuring the visual characteristics of a surface including:
    A. An illumination system comprising:
        a light source for providing an incident beam of light; and
        a scanner including a mirror disposed to intercept said incident beam of light and direct it onto a surface to be characterized so as to produce a reflected beam of light, said scanner further including a scan mechanism for moving said mirror so as to scan said incident beam of light across said surface; said apparatus further including,
    B. A measuring system comprising:
        a beam splitter disposed and operative to intercept said reflected beam and to split it into a first portion and a second portion;
        a control sensor which is disposed on a support member and positioned so as to intercept said first portion of said reflected beam and is operative to generate a control signal which corresponds to a spatial profile of said first portion;
        a measuring sensor which is disposed so as to intercept said second portion of said reflected beam and is operative to generate an output signal corresponding to said second portion;

a field mask which is supported on said support member in a fixed positional relationship with said control sensor, and is interposed in said second portion of said reflected beam, said field mask defining an aperture which permits only a segment of the cross-sectional area of said second portion of said reflected beam to pass therethrough and be incident upon said measuring sensor;

a tracking driver which is operative to receive said control signal and spatially displace said support member, control sensor and field mask in response thereto so as to establish a feedback loop between said control sensor and tracking driver wherein the tracking driver displaces the control sensor relative to the first portion of the reflected beam so as to maintain a preselected spatial relationship between the first portion of the beam and the control sensor, and wherein said field mask is also spatially displaced relative to the second portion of the reflected beam.

17. A method for characterizing the haze of a finished surface, said method comprising the steps of:

providing a light source;

projecting an incident beam of light from said source onto an object to be characterized, for reflection thereby, so as to provide a reflected beam of light, said reflected beam of light having a cross-sectional area;

disposing a photo sensor in said reflected beam of light, said photo sensor being operative to provide an output signal proportional to the intensity of the reflected beam of light incident thereupon;

interposing a field mask in said reflected beam of light between the surface and the photo sensor, said field mask having an aperture defined therethrough, said aperture having an area which is less than the cross-sectional area of the beam of reflected light;

moving the field mask transversely through the reflected beam so as to sequentially pass portions of the cross-sectional area of the reflected beam therethrough and onto the photo sensor; and determining the rate of change of the output signal of said photo sensor, as said field mask is moved, whereby the rate of change of said output signal is proportional to the haze of said surface.

18. A method as in claim 17, including the further step of scanning said incident beam of light along said surface in a linear direction, wherein the step of moving said field mask transversely through said reflected beam comprises moving said field mask through said reflected beam at an angle relative to said linear path of travel.

* * * * *